United States Patent [19]

Amemiya et al.

[11] Patent Number: 4,866,613
[45] Date of Patent: Sep. 12, 1989

[54] ULTRASONIC CONTINUOUS WAVE BLOOD FLOWMETER USING DOPPLER EFFECT ANALYSIS

[75] Inventors: Shin-ichi Amemiya, Yokohama; Kenji Ishiwata, Kawasaki, both of Japan

[73] Assignee: Fujitsu Limited, Kawasaki, Japan

[21] Appl. No.: 129,846

[22] Filed: Dec. 8, 1987

[30] Foreign Application Priority Data

Dec. 18, 1986 [JP] Japan .............................. 61-302178

[51] Int. Cl.⁴ .............................................. H03B 1/00
[52] U.S. Cl. ......................... 364/413.25; 73/861.25; 128/661.08; 128/662.01; 364/413.07
[58] Field of Search ...................... 364/724.19, 724.18, 364/825, 413.07, 413.25; 128/662.01, 661.08, 661.09, 661.02; 328/167; 73/861.25

[56] References Cited

U.S. PATENT DOCUMENTS

| | | | |
|---|---|---|---|
| 4,039,980 | 5/1972 | Nagahama | 333/174 |
| 4,423,488 | 12/1983 | Campbell | 364/724.18 |
| 4,540,946 | 9/1985 | Lainz et al. | 128/661.08 |
| 4,770,185 | 9/1988 | Silverstein et al. | 128/661.08 |

FOREIGN PATENT DOCUMENTS

0172687 2/1986 European Pat. Off. .

*Primary Examiner*—Jerry Smith
*Assistant Examiner*—Kim Thanh Tbui
*Attorney, Agent, or Firm*—Staas & Halsey

[57] ABSTRACT

An ultrasonic continuous wave blood flowmeter using Doppler effect analysis includes a filter having a cut-off frequency determined in part by a manually selected zero shift value. A tranducing device, in the flowmeter includes a transmission element and a reception element, the transmission element transducing an electric transmission signal into an ultrasonic signal to irradiate a living body and the reception element transducing a reflected ultrasonic signal into an electric reception signal. A detecting circuit is operatively connected to the transducing device for orthogonally detecting the electric reception signal and outputting a Doppler detection signal. A filter circuit is operatively connected to the detecting circuit for cutting high frequency components of the Doppler detection signal based on the cut-off frequency and outputting an analog signal. A converting circuit is operatively connected to the filter circuit for converting the analog signal of the filter circuit to a digital signal based on a Doppler sampling frequency having a continuous wave. A transforming circuit is operatively connected to the converting circuit for analyzing the digital signal and obtaining a Doppler frequency spectrum based on a Fourier transform method. A control circuit is operatively connected to the filter circuit for controlling the cut-off frequency based on the Doppler sampling frequency and the zero shift value.

5 Claims, 6 Drawing Sheets

ULTRASONIC CONTINUOUS WAVE BLOOD FLOWMETER USING DOPPLER EFFECT ANALYSIS

BACKGROUND OF THE INVENTION

1. Field of the Invention

The present invention relates to a blood flowmeter. More particularly, it relates to the blood flowmeter utilizing an ultrasonic continuous wave and having a Doppler effect.

2. Description of the Related Art

Blood flowmeters are widely used in the diagnosis of a living body, in the field of medical instruments, and are able to measure blood stream volume and distribution flowing in a blood vessel without exposure or cutting of the blood vessel.

Two known types of blood flowmeters utilize an electromagnetic effect and an ultrasonic wave, and these types of blood flowmeters basically have the same structure as that of a flowmeter used as industrial equipment. In a blood flowmeter using an ultrasonic wave, a Doppler effect is generally utilized for measuring blood stream volume. That is, the blood stream volume can be obtained by irradiating the ultrasonic wave and measuring the frequency shift quantity between a reflected wave and a transmitted wave.

There are two types of ultrasonic waves used in this field, a pulse wave and a continuous wave (CW). The present invention refers to the CW type ultrasonic wave device.

SUMMARY OF THE INVENTION

The object of the present invention is to provide an improved ultrasonic, CW blood flowmeter having a Doppler effect and enabling the production of a high quality Doppler signal having an improved signal to noise ratio (S/N) by reducing thermal noise.

In accordance with the present invention, there is provided an ultrasonic continuous wave blood flowmeter having a Doppler effect, comprising: a transducing device having a transmission element and a reception element, the transmission element transducing an electric transmission signal to an ultrasonic signal to irradiate a living body, and the reception element transducing a reflected ultrasonic signal to an electric reception signal; a detecting circuit operatively connected to the transducing element for orthogonally detecting the electric reception signal and outputting a Doppler detection signal; a filter circuit operatively connected to the detecting circuit, for cutting high frequency components of the Doppler detection signal based on a cut-off frequency and outputting an analog signal; a converting circuit operatively connected to the filter circuit, for converting the analog signal of the filter circuit to a digital signal based on a Doppler sampling frequency having a continuous wave; a transforming circuit operatively connected to the converting circuit, for analyzing the digital signal and obtaining a Doppler frequency spectrum based on a Fourier transform method; and a control circuit operatively connected to the filter circuit, for controlling the cut-off frequency based on the Doppler sampling frequency and a zero shift value decided manually.

DESCRIPTION OF THE PREFERRED EMBODIMENTS

Before describing the preferred embodiments, an explanation will be given of a conventional ultrasonic CW blood flowmeter having a Doppler effect (hereinafter, Doppler blood flowmeter).

Figure 1:
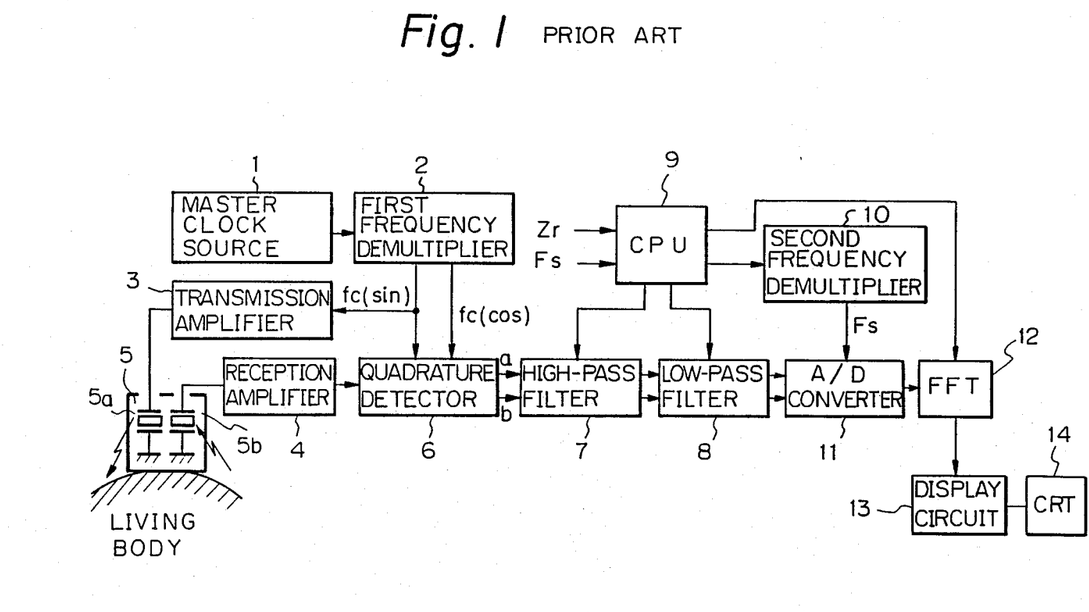
FIG. 1 is a schematic block diagram of a conventional ultrasonic CW blood flowmeter having a Doppler effect.

In FIG. 1, reference number 1 denotes a master clock source, 2 a first frequency demultiplier, 3 a transmission amplifier, 4 a reception amplifier, 5 a probe, 6 a quadrature detector, 7 a high-pass filter, 8 a low-pass filter, 9 a central processing unit, 10 a second frequency demultiplier, 11 an analog-to-digital converter, 12 a fast Fourier transformer, 13 a display circuit, and 14 a cathode-ray tube.

The probe 5 is constituted by a split type ultrasonic transducer, consisting of a transmission element 5a and a reception element 5b. The probe 5 is placed in contact with a living body (below the curved line) when measuring the blood flow therein. The master clock source 1 generates a master clock signal and the master clock signal is demultiplied by the frequency demultiplier 2. The demultiplied frequency signal fc(sin) is applied to the transmission element 5a through the transmission amplifier 3. The transmission element 5a converts the demultiplied frequency signal, i.e., the electric transmission signal, to an ultrasonic signal, and this ultrasonic signal is then transmitted into the living body. An ultrasonic signal reflected from the blood vessel is received by the reception element 5b, which converts the reflected ultrasonic signal to an electric reception signal. The electric reception signal is input to the quadrature detector 6 through the reception amplifier 4. In the quadrature detector 6, the electric reception signal is detected by the heterodyne detection method based on the generated signals fc(sin) and an orthogonal generated signal fc(cos), both output by the frequency demultiplier 2. When the difference be the transmitted signal and the reception signal is shifted to zero, Doppler detection signals (a and b) can be obtained from the quadrature detector 6. In this case, the output signals a and b are orthogonal to each other, and therefore, the signals a and b are used to distinguish between plus side frequency components and minus side frequency components. The quadrature detection is utilized for measuring the speed of the blood stream flowing toward the probe 5 and flowing away from the probe 5. A quadrature detection signal (Doppler detection signal) is input to the high-pass filter 7 and the low frequency components are cut by this filter 7. The cut-off frequency of the filter 7 is decided based on a position to be measured on the living body. That is, the cut-off frequency is set so as to eliminate low frequency components mainly caused by vibration of a wall of the blood vessel.

Conventionally, the high-pass filter 7 is constituted by a plurality of filter units, and each of the filter units is controlled by analog switches selected by the central processing unit 9.

An analog signal passed through the high-pass filter 7 is input to the low-pass filter 8. A cut-off frequency of the low-pass filter 8 is set in correspondence with a Doppler sampling frequency Fs input to the analog-to-digital (A/D) converter 11, and unnecessary frequency components are eliminated through the low-pass filter 8. The Doppler sampling frequency Fs is generated from the second frequency demultiplier 10. The low-pass filter 8 is constituted by a plurality of filter units, and each of the filter units is selected by the central processing unit 9 in correspondence with the Doppler sampling frequency Fs input to the A/D converter 11. A signal converted by the A/D converter 11 is input to the fast Fourier transformer (FFT) 12 and converted from time base signals to frequency base signals. The frequency power spectrum of the Doppler signal is displayed on the display device (CRT) 14 through the display circuit 13 for an intensity modulation.

Figure 2:
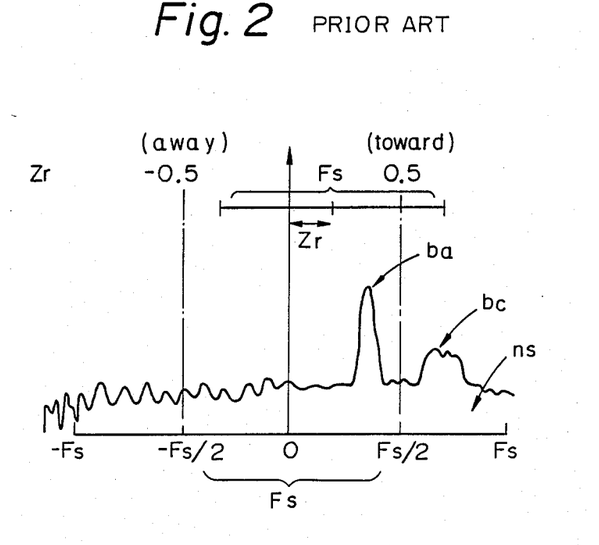
FIG. 2 is a view for explaining a frequency shift quantity in FIG. 1.

In FIG. 2, the ordinate denotes an intensity (amplitude), and the abscissa denotes the frequency shift quantity. This frequency shift quantity corresponds to the blood stream volume (speed) ad distribution. The cut-off frequency of the low-pass filter 8 is generally decided by a half of the Doppler sampling frequency Fs based on the "Nyquist theorem". In this case, although the display area on the CRT becomes between $-Fs/2$ and $Fs/2$ with respect to the center frequency "0", when the center frequency is shifted from "0" by the zero shift value Zr due to a faster blood stream speed, the new display area changes to between $(-Fs/2-Zr)$ and $(Fs/2+Zr)$. Initially, the zero shift value Zr is manually set and controlled by the CPU 9 by changing a read-out start address of the frequency spectrum analyzed by the FFT 12. In FIG. 2, ba and bc denote blood signals, and ns denotes a noise signal. As is clear from the drawing, the blood signal ba can be displayed on the CRT because this signal ba exists in the extent of the cut-off frequency $Fs/2$ of the low-pass filter 8. However, the blood signal bc cannot be displayed on the CRT because this signal bc exists outside of the cut-off frequency $Fs/2$.

Figure 3:
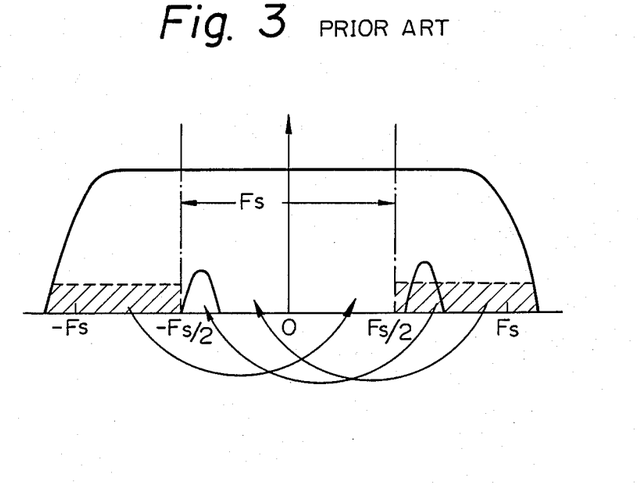
FIG. 3 is a view for explaining a cut-off frequency in FIG. 1.

In FIG. 3, the cut-off frequency of the low-pass filter 8 is newly set to the same frequency as the Doppler sampling frequency Fs. That is, the new cut-off frequency Fs is decided on the basis that the maximum value of the zero shift value Zr can be changed between $Fs/2$ and $-Fs/2$. Therefore, the signal can be passed between $-Fs$ and $Fs$.

In this case, as shown by arrows, the signal components between $Fs/2$ and $Fs$ can be folded to the area between $-Fs/2$ and 0, and the signal components between $-Fs/2$ and 0 can be also folded to the area between $Fs/2$ and $Fs$. Similarly, the signal components between $-Fs$ and $-Fs/2$ can be folded to the area between 0 and $Fs/2$. The above folding can be performed based on a "folding phenomena" of the FFT 12 in the Doppler sampling frequency Fs. Note: The "folding phenomena" is a well known analysis method carried out on the Fourier domain. Therefore, a detailed explanation thereof is omitted in this specification. Therefore, the signal components beyond the area between $-Fs/2$ and $Fs/2$ can be detected by using the zero shift function utilizing the "folding phenomena".

Conversely, when the zero shift is not done, the unnecessary signal components between $-Fs$ and $-Fs/2$, and between $Fs/2$ and $Fs$ are also input. Therefore, the thermal noise (hashed area in FIG. 3) is also superposed on the Doppler signal so that the S/N ratio is worsened. In this case, the thermal noise depends on the resistance components of the transducers 5a and 5b, and this noise is peculiar to the resistance components and can not be eliminated.

Figure 4:
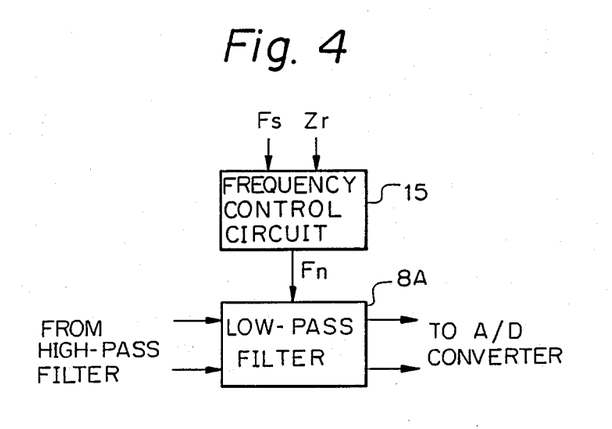
FIG. 4 is a principal block diagram of an ultrasonic CW blood flowmeter having a Doppler effect according to the present invention.
Figure 6:
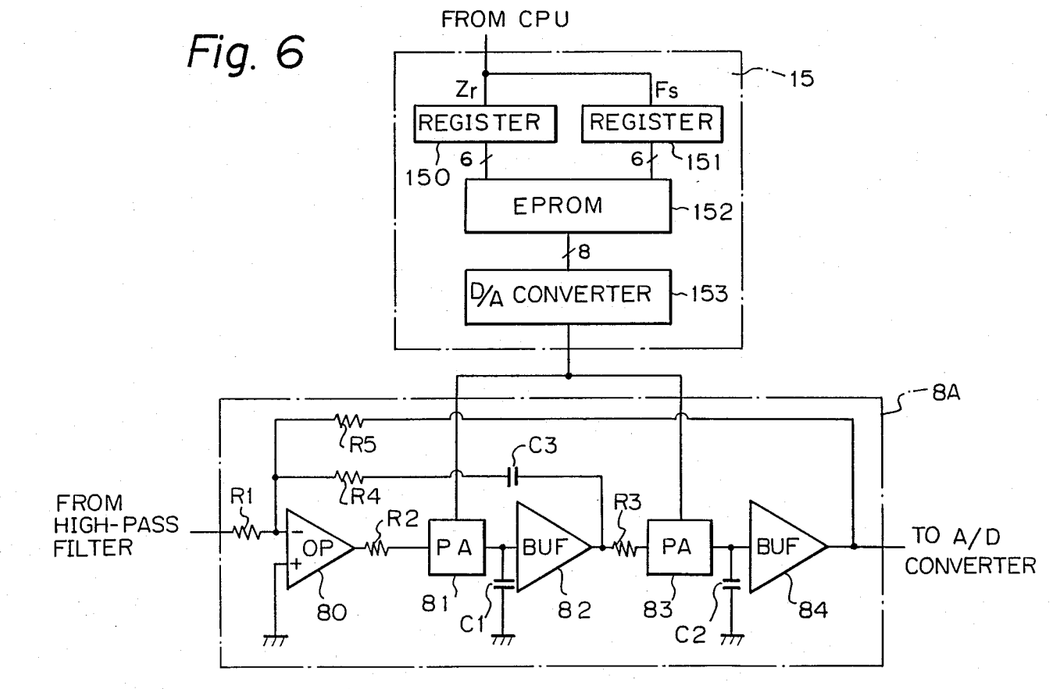
FIG. 6 is a detailed circuit diagram according to an embodiment of the present invention shown in FIG. 4.

An ultrasonic CW Doppler blood flowmeter according to the present invention will be explained in detail hereinafter. In FIG. 4, 8A is a low-pass filter according to the present invention and a detailed circuit diagram as one embodiment is shown in FIG. 6. Reference number 15 is a frequency control circuit (FCC) according to the present invention and a detailed block diagram as one embodiment is also shown in FIG. 6. The new low-pass filter 8A is provided instead of the conventional low-pass filter 8 shown in FIG. 1. Further, the frequency control circuit 15 is provided between the CPU 9 and the low-pass filter 8A. The cut-off frequency Fm of the low-pass filter 8A is variable and is controlled by a control signal Fn from the frequency control circuit 15 based on the zero shift value Zr and the Doppler sampling frequency Fs of the continuous wave (CW). That is, although a primary element deciding the cut-off frequency is only given by the CW Doppler sampling frequency Fs in the conventional method, it is given by the CW Doppler sampling frequency Fs and the zero shift value Zr in the present invention.

Figure 5:
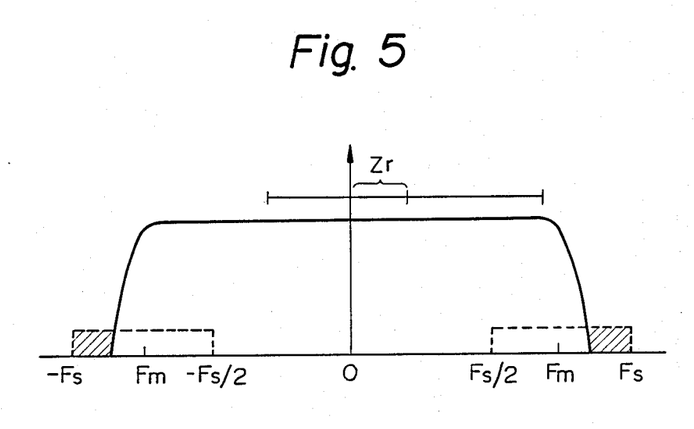
FIG. 5 is a view for explaining a cut-off frequency in FIG. 4.

In FIG. 5, the cut-off frequency Fm is given as follows.

$$Fm = Fs/2 + |Zr|$$

where $|Zr|$ is an absolute value of the zero shift value. As is obvious from the above formula, the cut-off frequency Fm is variable dependent on the zero shift value Zr in the extent between $Fs/2$ and $Fs$. The thermal noise can be eliminated from the, cut-off frequency Fm, as shown by the hashed area.

In FIG. 6, although the low-pass filter 8A is shown for only one channel, actually, two channels are necessary because the outputs of the quadrature detector 6 are the orthogonal signals a and b. However, the other channel side is omitted in order to simplify the explanation. R1 denotes an input resistor, R2 and R3 integrating circuit resistors, R4 and R5 feedback resistors, C1 and C2 integration circuit capacitors, C3 a feedback capacitor, 80 an operational amplifier (OP), 81 and 83 voltage controlled attenuators (PA), and 82 and 84 buffer amplifiers (BUF). Each voltage controlled attenuator 81, 83 is constituted by a variable resistor and the input current is attenuated by the gain corresponding to the control voltage from the frequency control circuit 15.

The frequency control circuit 15 is constituted by registers 150 and 151, an erasable programmable read only memory (EPROM) 152, and a digital-to-analog (D/A) converter 153. The registers 150, 151 temporarily store the zero shift value Zr having six bits and the CW Doppler sampling frequency Fs having six bits, both applied from the CPU 9. The EPROM 152 stores a digital voltage to set the cut-off frequency Fm in the low-pass filter 8A corresponding to the zero shift value Zr and the CW Doppler sampling frequency Fs. The D/A converter 153 converts the digital voltage having eight bits to an analog voltage and outputs it to the voltage controlled attenuators 81 and 83.

Figure 7:
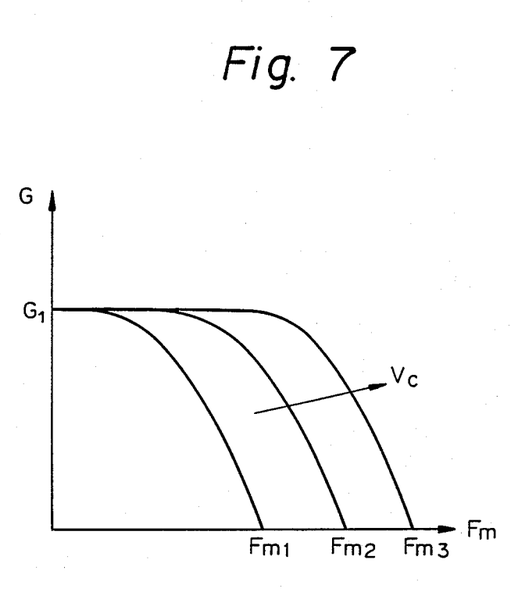
FIG. 7 is a view for explaining a relationship between a control voltage and a cut-off frequency.

The explanations of these circuits will be given in detail with reference to FIG. 7. In FIG. 7, the ordinate G denotes a gain and the abscissa Fm a cut-off frequency. The low-pass filter 8A comprises two stage integration circuits, each connected to the attenuator (81 and C1, 83 and C2). Each of the integration circuits is controlled by the feedback loops through the feedback resistors R4 and R5. The integration circuit usually has a filtering function, and therefore, the low-pass filter 8A also has the filtering function of passing the low frequency based on the control of the input voltage to the voltage controlled attenuators 81 and 83.

The zero shift value Zr and the CW Doppler sampling frequency Fs are manually set in a control panel (not shown). The CPU 9 sets these values to the registers 150 and 151. The cut-off frequency Fm is set based on the above formula for the value Zr and the frequency Fs in the EPROM 152. The EPROM 152 outputs the digital voltage corresponding to the cut-off frequency Fm, and the output digital voltage is converted to the analog value in the D/A converter 153. The analog voltage is output to the voltage controlled attenuators 81 and 83 as the control voltage Vc.

Therefore, as shown in FIG. 7, the gain G is controlled to a constant value G1 when the control voltage Vc is increased as indicated by the arrow. The cut-off frequency Fm is changed to the frequencies $Fm_1$, $Fm_2$ and $Fm_3$ in correspondence with the change of the control voltage Vc. Accordingly, since it is possible to set the passing band corresponding to the zero shift value Zr and the CW Doppler sampling frequency Fs in the low-pass filter 8A, it is also possible to obtain the Doppler signal having the improved S/N ratio from which unnecessary thermal noise has been eliminated.

Consequently, this unnecessary thermal noise is not contained in the Doppler detection signal at the display CRT as shown in FIG. 5, and the zero shift function can be maintained, and therefore, it is possible to easily measure the blood stream speed and distribution, to achieve a very precise diagnosis of the living body.

In the above embodiment, although the frequency control circuit 15 is provided to an external stage of the CPU 9, it is possible to insert the same function as this circuit in the CPU 9. Further, it is possible to provide a plurality of filters corresponding to the sampling frequency Fs instead of the low-pass filter 8A which can change the cut-off frequency.

Figure 8:
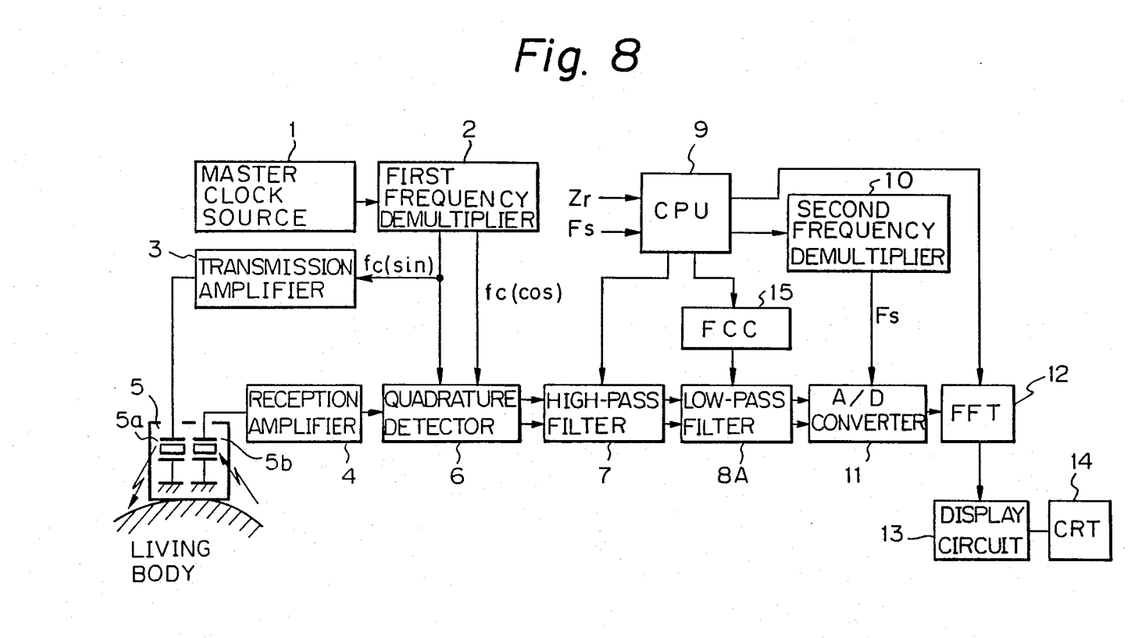
FIG. 8 is a schematic block diagram of an ultrasonic CW blood flowmeter having a Doppler effect according to an embodiment of the present invention.

In FIG. 8, the frequency control circuit 15 is connected in series between the CPU 9 and the low-pass filter 8A as explained in FIG. 4. Since the operations of this block diagram are referred to above, the explanation is omitted.

What is claimed is:

1. An ultrasonic continuous wave blood flowmeter using Doppler effect analysis on ultrasonic signals echoed from a living body, comprising:
    transducing means, having a transmission element and a reception element, for outputting an ultrasonic signal to irradiate the living body and for transducing a reflected ultrasonic signal from the living body into an electric reception signal;
    detecting means, operatively connecting to said transducing means, for orthogonally detecting the electric reception signal and for outputting a Doppler detection signal;
    "filter means, operatively connected to said detecting means, for cutting high frequency components of the Doppler detection" signal above a cut-off frequency and for outputting an analog signal;
    converting means, operatively connected to said filter means, for converting the analog signal of said filter means to a digital signal based on a Doppler sampling frequency having a continuous wave;
    transforming means, operatively connected to said converting means, for analyzing the digital signal to obtain a Doppler frequency spectrum based on a Fourier transform method, the Doppler frequency spectrum including a representation of bloodstream distribution in the living body; and
    control means, operatively connected to said filter means, for controlling the cut-off frequency based on the Doppler sampling frequency and a zero shift value decided manually, the zero shift value determining an extent of the Doppler frequency spectrum to be displayed.

2. An ultrasonic continuous wave blood flowmeter using Doppler effect analysis on ultrasonic signals echoed from a living body, comprising:
    transducing means, having a transmission element and a reception element, for outputting an ultrasonic signal to irradiate the living body and for transducing a reflected ultrasonic signal from the living body into an electric reception signal;
    detecting means, operatively connected to said transducing means, for orthogonally detecting the electric reception signal and for outputting a Doppler detection signal;
    filter means, operatively connected to said detecting means, for cutting high frequency components of the Doppler detection signal above a cut-off frequency and for outputting an analog signal;
    converting means, operatively connected to said filter means, for converting the analog signal of said filter means to a digital signal based on a Doppler sampling frequency having a continuous wave;
    transforming means, operatively connected to said converting means, for analyzing the digital signal to obtain a Doppler frequency spectrum based on a Fourier transform method; and
    control means, operatively connected to said filter means, for controlling the cut-off frequency based on the Doppler sampling frequency and a zero shift value decided manually, said control means comprising:
    a first register for temporarily storing the zero shift value;
    a second register for temporarily storing the Doppler sampling frequency;
    an erasable programmable read only memory, operatively connected to said first and second registers, for storing a relationship to convert from the zero shift value and the Doppler sampling frequency to a digital value representing the cut-off frequency; and
    a digital-to-analog converter, operatively connected to said erasable programmable read only memory and said filter means, for converting the digital value to an analog voltage for controlling said filter means.

3. An ultrasonic continuous wave blood flowmeter for detecting blood flow in a living body, comprising:
control means including means for storing a Doppler sampling frequency and a zero shift value, both manually set by an operator;
Doppler signal means for irradiating the living body with an ultransonic signal and for detecting echoes of the ultrasonic signal emanating from the living body to produce a Doppler detection signal;
filter means for cutting high frequency components of the Doppler detection signal above a cut-off frequency determined in dependence upon the Doppler sampling frequency and the zero shift value to produce a filtered signal; and
analysis means for analyzing the filtered signal to obtain a Doppler frequency spectrum including a representation of bloodstream distribution in the living body, the Doppler frequency spectrum having a range partially determined by the zero shift value.

4. An ultrasonic continuous wave blood flowmeter as claimed in claim 3, wherein said filter means comprises:
converter means for converting the Doppler sampling frequency and the zero shift value into an analog voltage; and
low-pass filter means for filtering the high frequency components of the Doppler detection signal above the cut-off frequency, selected in dependence upon the analog voltage.

5. An ultrasonic continuous wave blood flowmeter as claimed in claim 4, wherein said low-pass filter means comprises:
operational amplifier means for amplifying the Doppler detection signal to produce an amplified signal;
at least one voltage controlled attenuator, operatively connected to said control means, said operational amplifier means and said analysis means, for attenuating the amplified signal by a gain determined in dependence upon the analog voltage to produce the filtered signal; and
feedback means for controlling frequency response provided by said operational amplifier means in dependence upon the filtered signal.

* * * * *